(12) United States Patent
Riquelme Salamanca et al.

(10) Patent No.: US 7,713,558 B2
(45) Date of Patent: May 11, 2010

(54) BACTERIAL PRODUCT FROM MARINE ORIGIN, USEFUL FOR PREVENTING THE MACRO AND MICRO BIOFOULING CAUSED BY MACROALGAE AND MARINE INVERTEBRATES

(75) Inventors: Carlos Eduardo Riquelme Salamanca, Antofagasta (CL); Fernando Rodrigo Silva Aciares, Antofagasta (CL); Marcela Clarke Guerra, Antofagasta (CL)

(73) Assignee: Universidad de Antofagasta, Antofagasta (CL)

(*) Notice: Subject to any disclaimer, the term of this patent is extended or adjusted under 35 U.S.C. 154(b) by 249 days.

(21) Appl. No.: 11/577,248

(22) PCT Filed: Oct. 14, 2005

(86) PCT No.: PCT/EP2005/011084

§ 371 (c)(1),
(2), (4) Date: Jul. 13, 2007

(87) PCT Pub. No.: WO2006/040174

PCT Pub. Date: Apr. 20, 2006

(65) Prior Publication Data

US 2008/0095871 A1    Apr. 24, 2008

(30) Foreign Application Priority Data

Oct. 15, 2004  (CL) ................................. 2658-2004

(51) Int. Cl.
*A61K 35/00*  (2006.01)

(52) U.S. Cl. ...................................................... 424/780
(58) Field of Classification Search ...................... None
See application file for complete search history.

(56) References Cited

FOREIGN PATENT DOCUMENTS

EP    1170359 A1    1/2002

OTHER PUBLICATIONS

Kon-ya, K. et al. Experientia, Birkhauser Verlag Base. (1995); 51:153-155. Inhibitory effect of bacterial ubiquinones on the settlin of barnacle, Balanus amphitrite.*
Hayase, Nobuki et al., Polymer Film Produced By A Marine Bacterium, Journal of Bioscience and Bioengineering, vol. 95, No. 1, pp. 72-76, 2003.
O'Conner, Nancy J. et al., Attachment of Barnacle (Balanus Amphitrite Darwin) Larvae: Responses to Bacterial Films and Extracellular Materials, Journal of Experimental Marine Biology and Ecology, vol. 226, pp. 115-129, Aug. 1, 1998.

* cited by examiner

*Primary Examiner*—Michele Flood
(74) *Attorney, Agent, or Firm*—Hasse & Nesbitt LLC; Daniel F. Nesbitt

(57) ABSTRACT

Extra-cellular product anti-biofouling against marine invertebrates which are common to the biofouling, which contains an extract of the supernatant of an *Alteromonas* sp. Culture. Anti-biofouling composition, comprising said extra-cellular product and a biopolymer. The use of said extra-cellular product for preparing a composition useful for inhibiting the marine micro- and macro-biofouling, and the process for preparing said extra-cellular product.

17 Claims, 16 Drawing Sheets

Adherence of *Navicula sp2*

Figure 1:
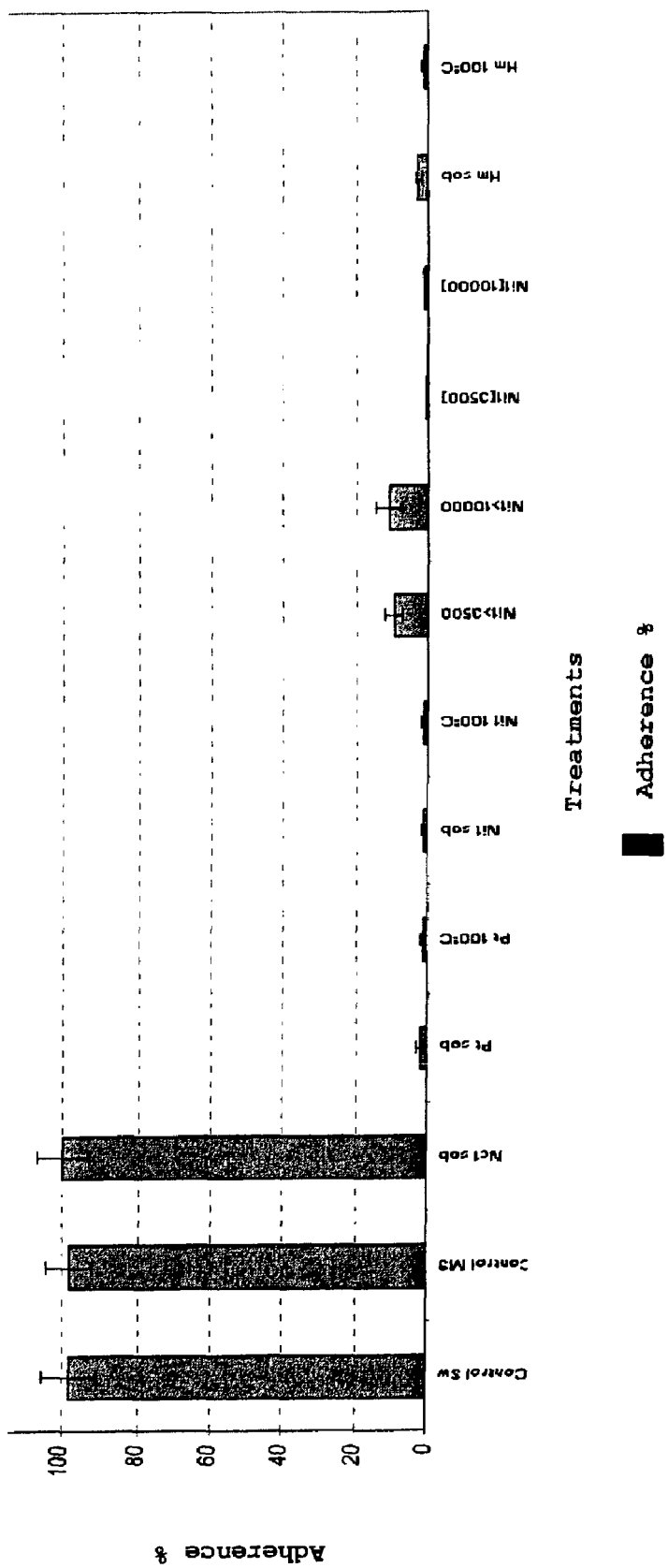
Figure 2:
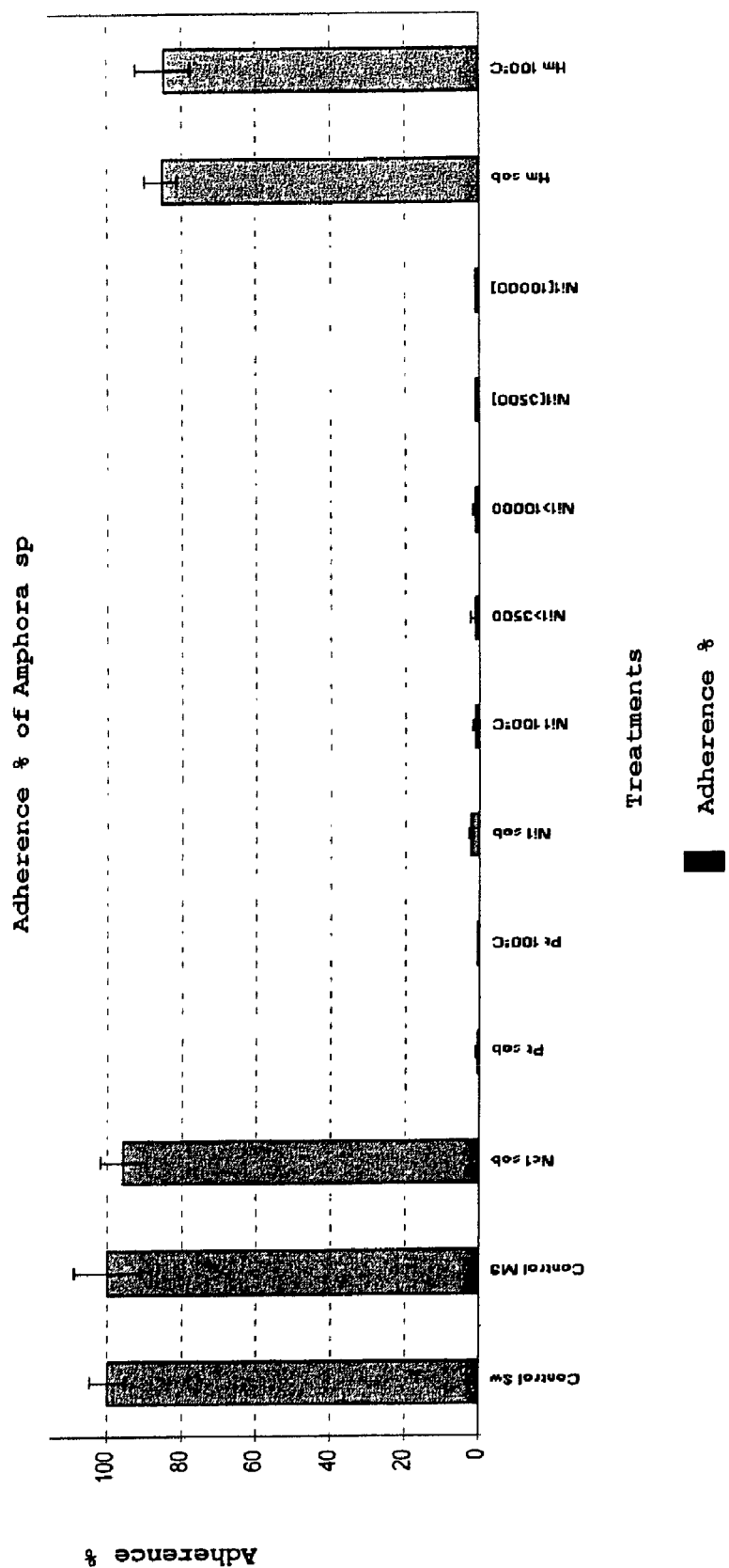
Figure 3:
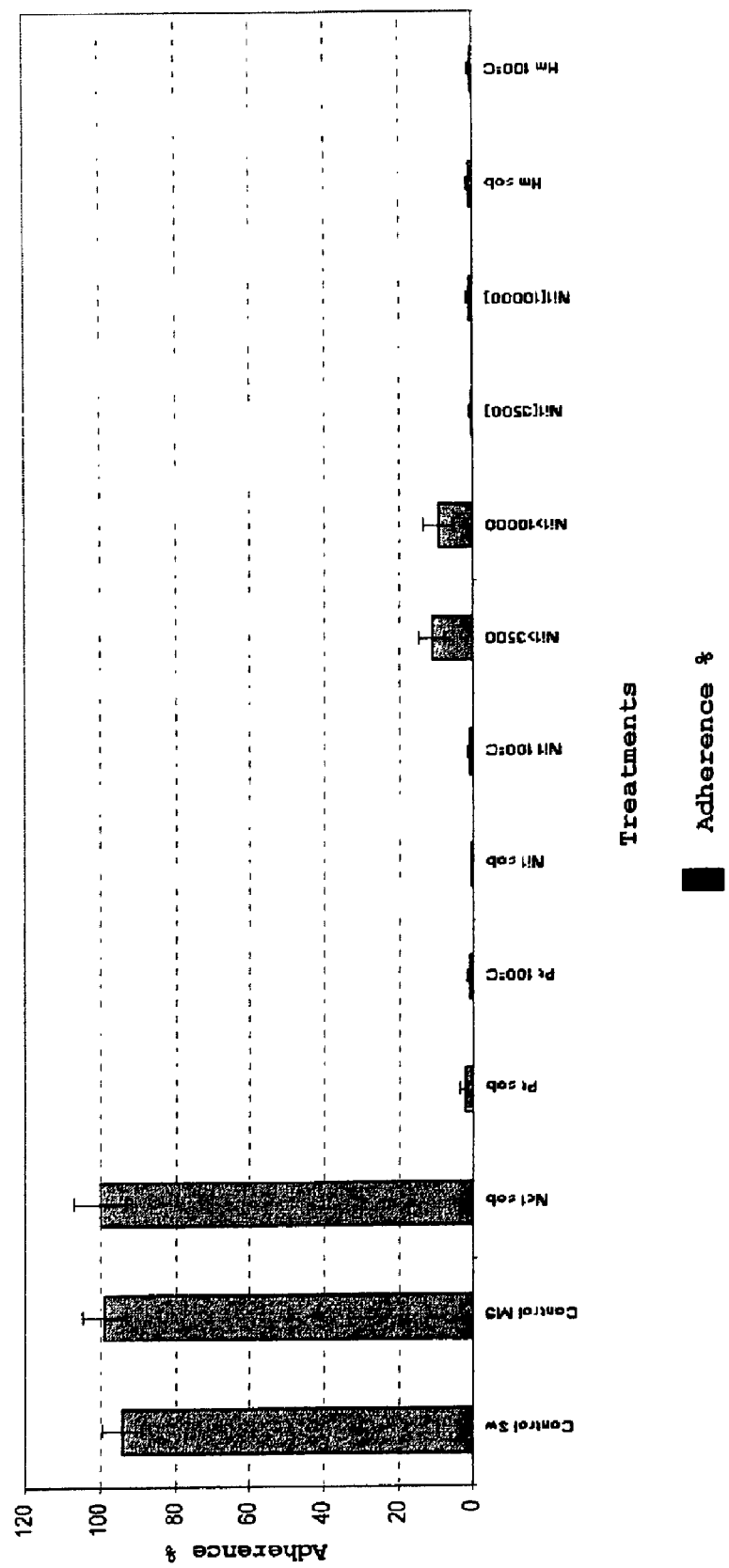
Figure 4:
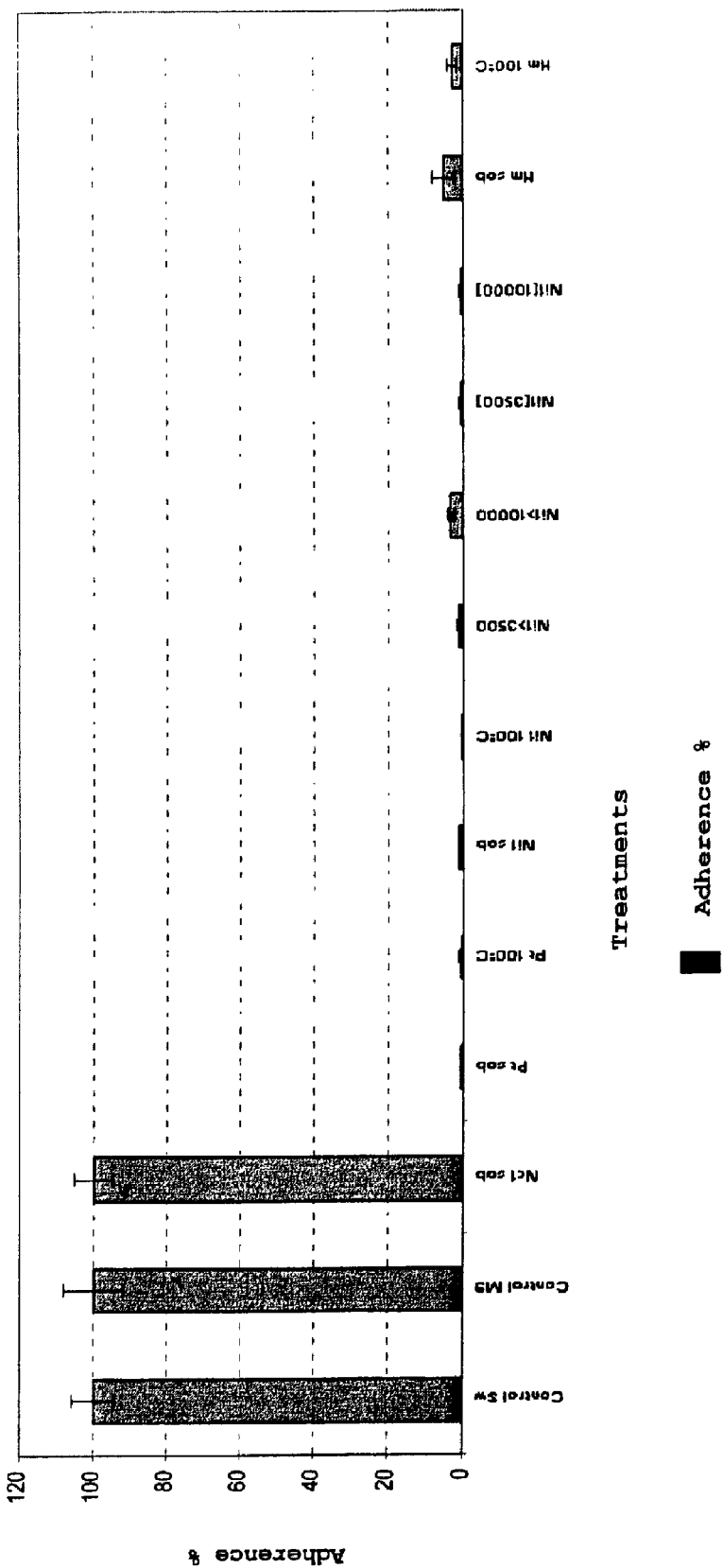
Figure 5:
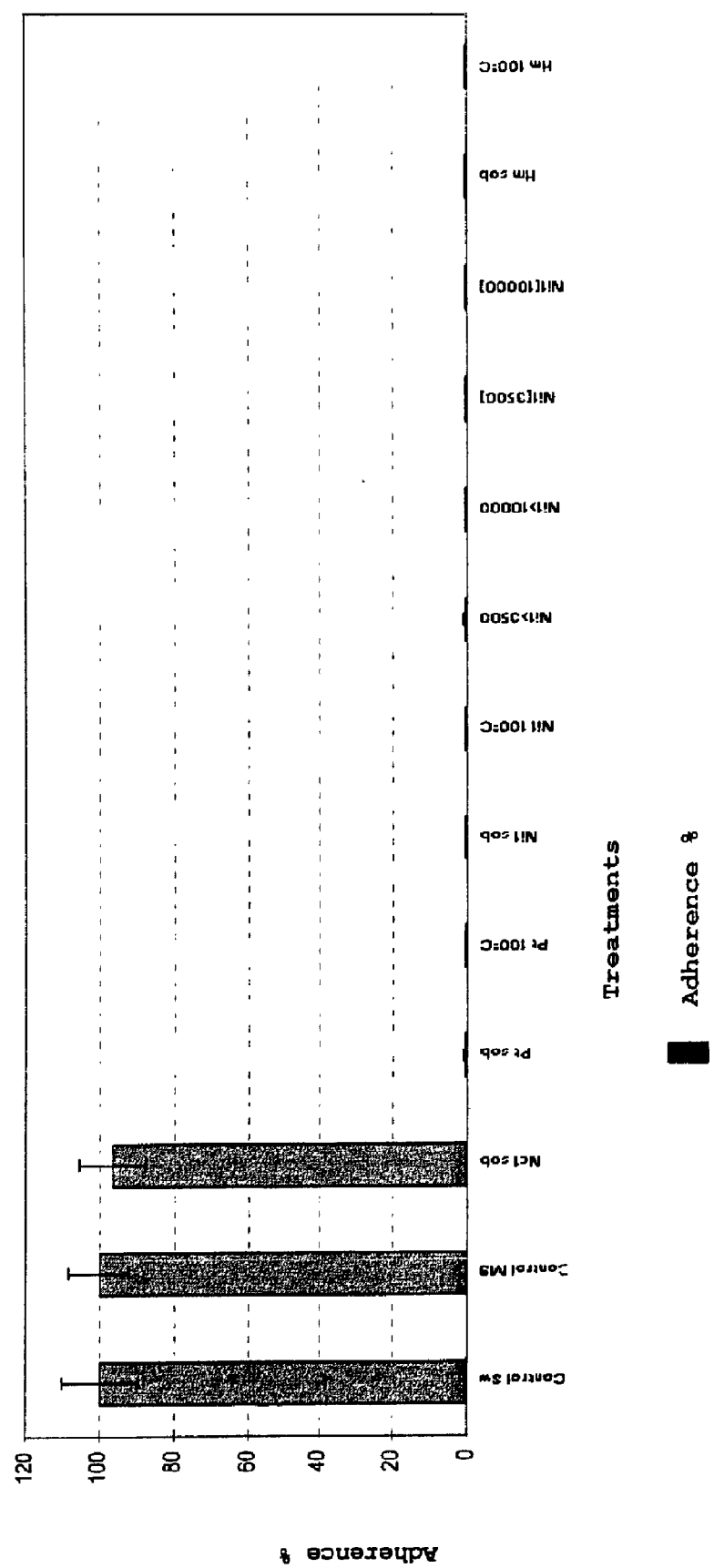
Figure 6:
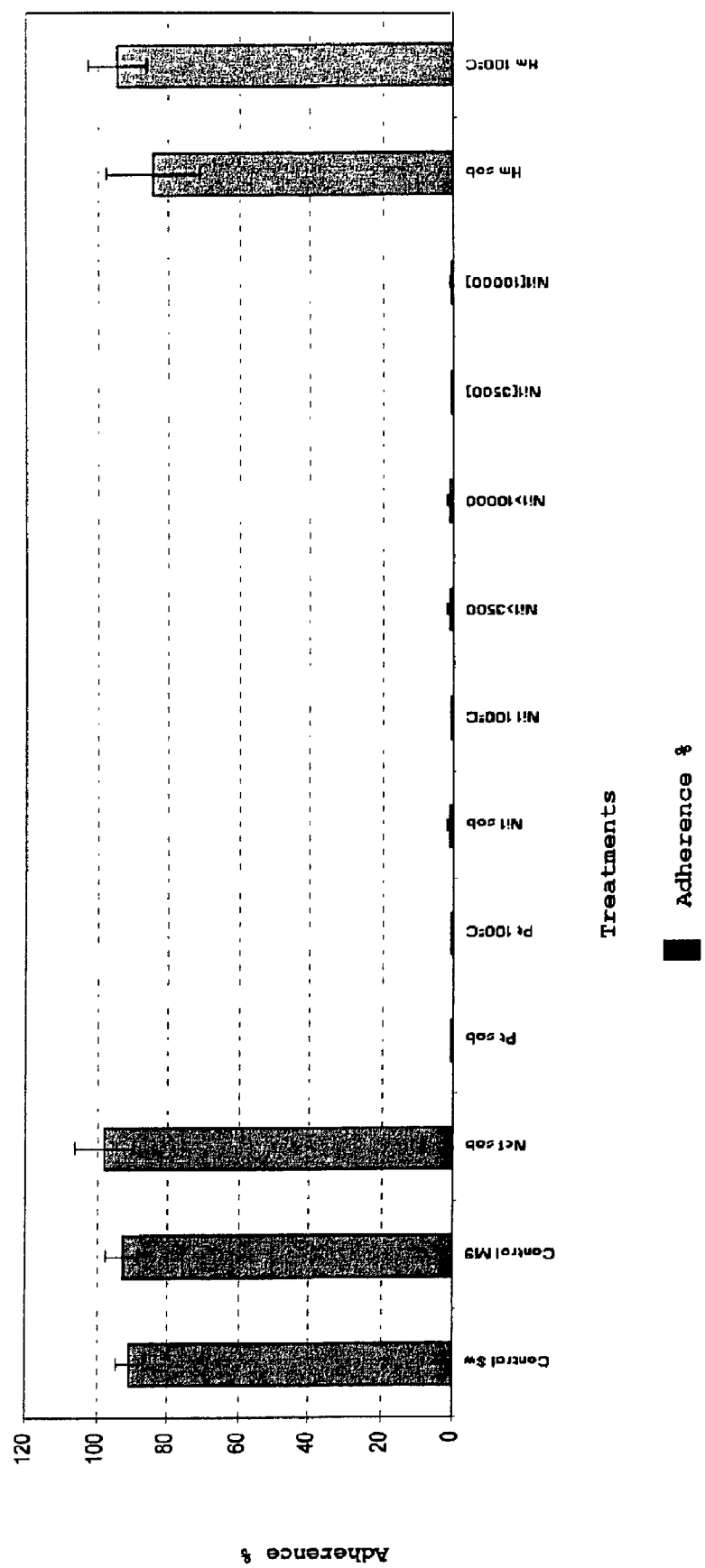
Figure 7:
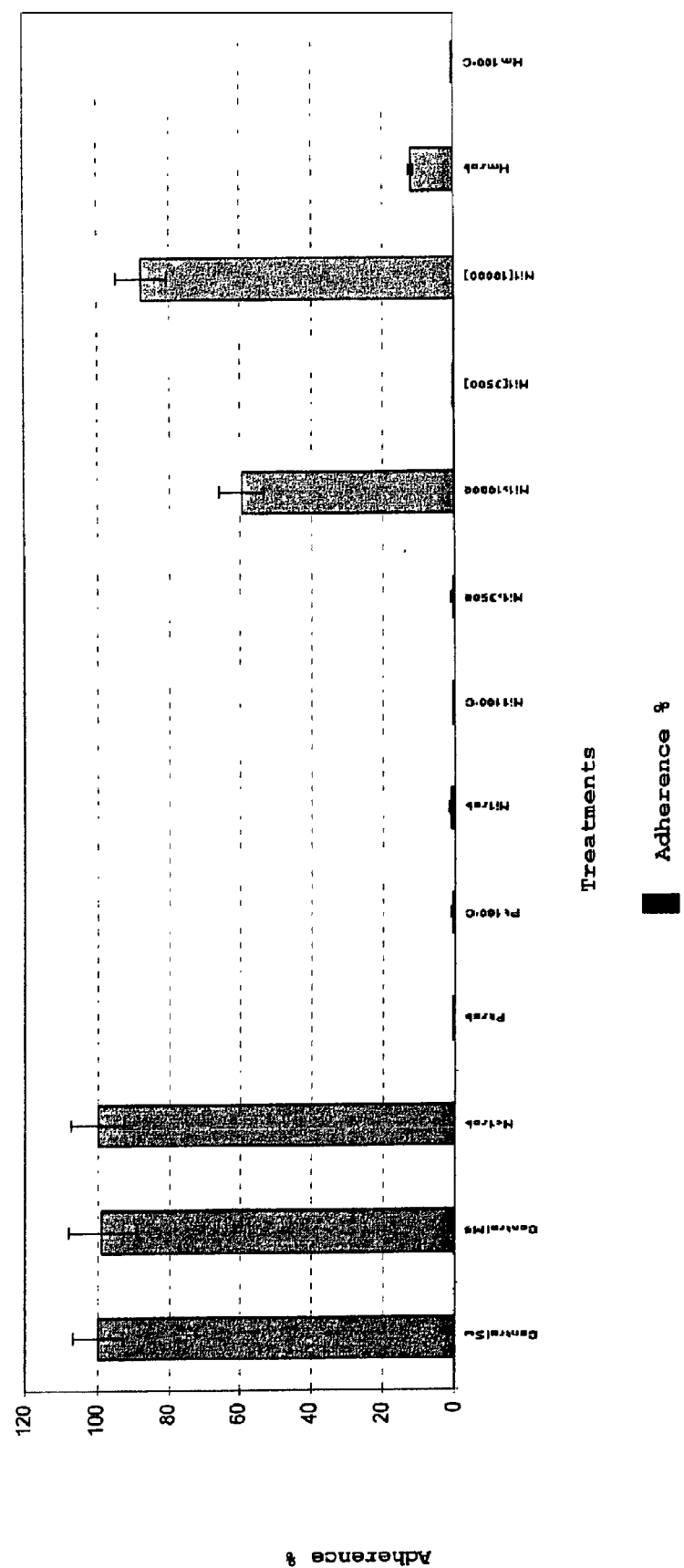
Figure 8:
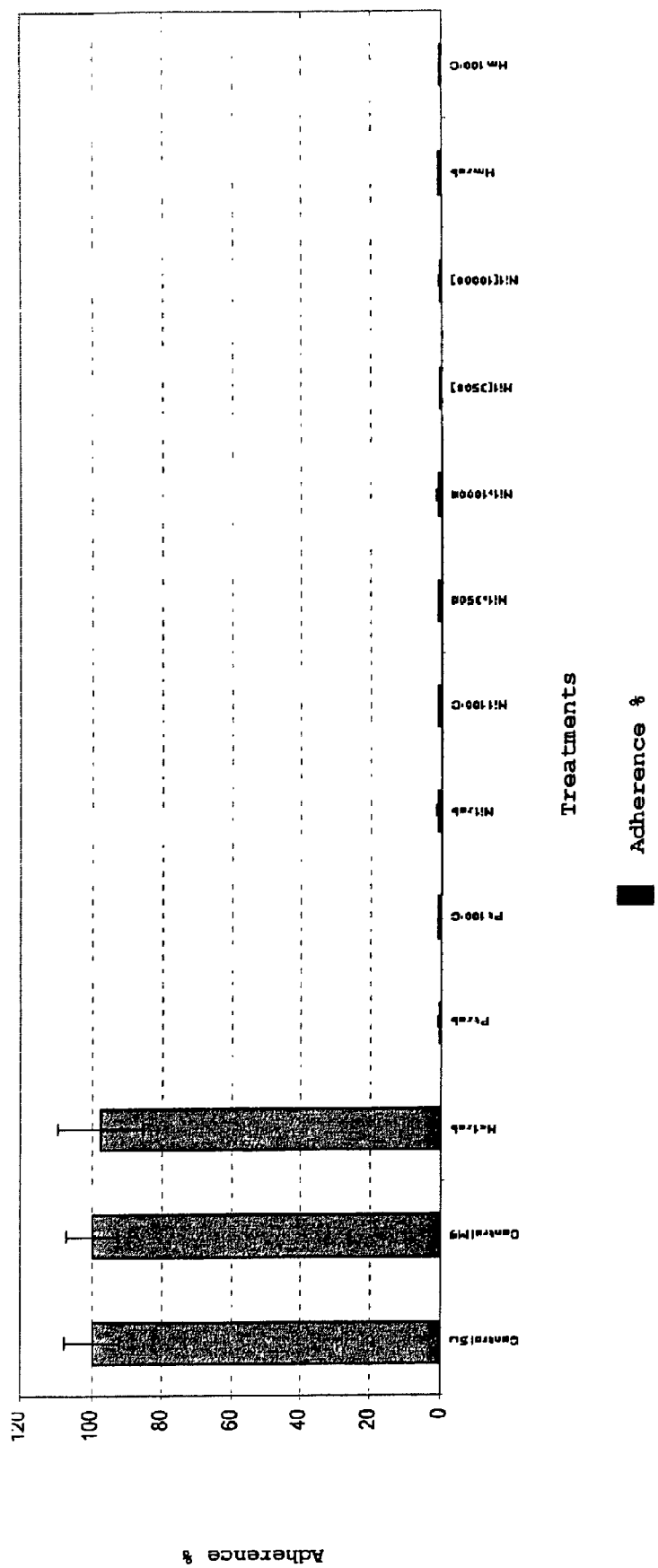

Effect of the bacterial extra-cellular products on the adherence of C. intestinalis larvae, at 48 hours of incubation Effect of the bacterial extra-cellular products on the adherence of Piuria preputialis larvae, at 24 hours of incubation Figure 16
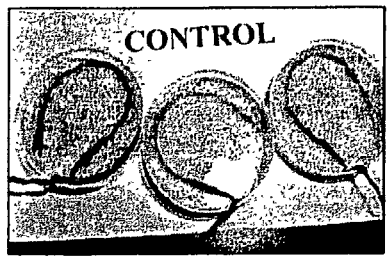
A) Control M9 at the second week.
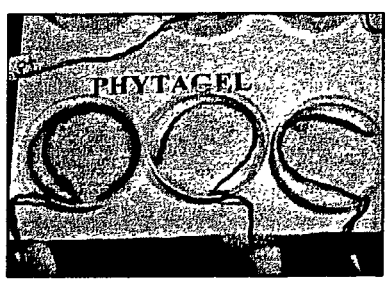
B) Phytagel Control at the second week.
C) Pt at the second week.
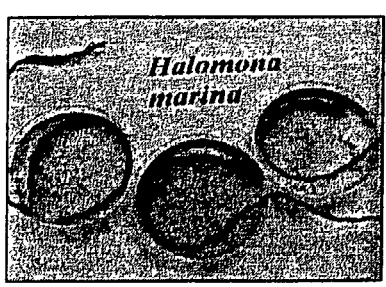
D) Hm at the second week.
E) Nil LEM at the second week.
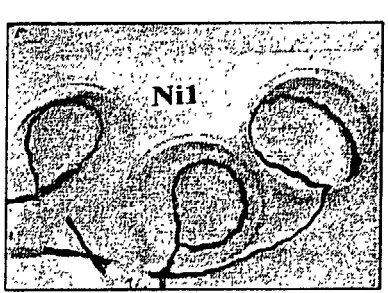

BACTERIAL PRODUCT FROM MARINE ORIGIN, USEFUL FOR PREVENTING THE MACRO AND MICRO BIOFOULING CAUSED BY MACROALGAE AND MARINE INVERTEBRATES

CROSS REFERENCE TO RELATED APPLICATIONS

This is the National Stage of International Application PCT/EP2005/011084, with an international filing date of Oct. 14, 2005.

TECHNICAL FIELD

The present invention relates to marine bacterial products, having inhibitory properties for the adherence or fixing of marine microalgae, macroalgae and invertebrates, which can fix or adhere on substrates, on a marine environment.

BACKGROUND OF THE INVENTION

The present invention describes extra-cellular bacterial products from a marine bacteria, *Alteromonas* sp, name as Ni1LEM, deposited at the Agricultural Research Culture Collection under the Accession No NRRL B-30784. Said extracts are useful for inhibiting the settlement and fixing of marine benthic microalgea (diatomeae), marine macroalgae and marine invertebrate larvae, mainly those that are involved on problems known as "biofouling", in the marine environment. Additionally, the present invention discloses the method for obtaining these extracts, which have biocide properties.

A surface, submerged on a marine ecosystem, is sensitive to be rapidly colonized. Said phenomenon is named "biofouling" or "bio-incrustation", which corresponds to the undesired accumulation of microorganisms, algae and animals on surfaces or structures submerged in the sea; in a first moment said phenomenon is initiated, by the origin of a film containing organic matter and dissolved macromolecules, such as polysaccharides, proteins and protein fragments, followed by bacteria, microalgae, protozoan, algae and invertebrates. Those organisms constituting the "biofouling" can be divided in "micro-biofouling" and "macro-biofouling". The micro-fouling or microbial films begin the colonization process on the exposed surfaces, after which occurs the colonization by the organisms that are responsible of the macro-biofouling (tunicates, balanides, mollusks and algae). Nevertheless, biofouling not only can be found non animated objects, but they can colonize the surface of marine plants and invertebrates. Some research studies have shown that the development of the biofouling on surfaces of non animated structures differs from the one of the colonized organisms, moreover the structures and constituents of the biofouling differ among one and other organism. However, at the sea, the marine algae and invertebrates are the main colonizers.

Substantial problems, to the structures submerged in the sea, are caused by the presence of "biofouling", resulting in economical loss. Among the main problems caused by "biofouling" on the marine environments, are those related to aquaculture and marine structure systems, such as the petroleum platform columns and boat hulls. Therefore, in aquaculture, per example, the accumulation of "biofouling" on the nets of the cages used for the fish culturing in aquaculture, provokes the sinking of the same, as well as the reduction of the water flux through the mesh, causing a drastic decrease of the concentration, within this culture systems, of the dissolved oxygen. Similar problems occur with those culture systems used in the filter feeding mollusks (scallops, oysters and mussels), wherein the organisms that are being cultured compete with the "biofouling" organisms for oxygen and nutrients. The above, generates the need of periodically removing the culture systems from the sea into the land for cleaning the same. This maintenance of the culturing material represents a high cost for the aquaculture companies. The problem of the "biofouling" phenomenon is not only restricted to the sea aquaculture systems, therefore this is the way how the land systems are not free of the problems caused by "biofouling". Per example, the tubes used for distributing the sea water for hatcheries of marine invertebrate's larvae and seed, of commercial importance, suffer the biologic colonization on their inner part, thus reducing the necessary pumping rate and the water flux.

For combating "biofouling" in marine structures, diverse toxic compounds have been used, being the most efficient, those compounds preferably based in tri-butyltin (TBT) or copper. These paints containing TBT are highly effective in the control of the biofouling in ships, achieving periods of seven years without requiring maintenance. Nevertheless, the environmental control policies have restricted the use of paints containing TBT in marine environments for crafts of more than 25 m of length, and due to its deleterious effects over the environment; the use of TBT should be eradicated on 2008. These rules are based on numerous studies about the effects of TBT, which have reported toxic effects, with so low concentrations, on marine organisms as mollusks.

One alternative for the paints containing TBT, are those in which the main constituent is copper and other heavy metals such as zinc. These paints are mainly used on small crafts, being effective during a period from 1 to 2 years. Nevertheless, government entities from several countries have indicated the risks of using these paints on the environment and the risk for the man, suggesting its prohibition. In this way, the International Maritime Organization has prohibited the use of tin in anti-biofouling paints from 2003 on. The use of copper in anti-biofouling paints is under a similar classification, being prohibited its use on the Baltic Sea from 2002 on. Copper, is toxic over some algae species and it is accumulated by those filter-feeding mollusks. It has been reported that a third part of the copper ions emission, on the north coast waters of Norway, come from anti-biofouling agents, used on aquaculture cages, a third part comes from the anti-biofouling paints used on craft hulls and the remaining third part from other sources. Nowadays, on Norway, the rules for the emission of these substances will produce a dramatic decrease of the emissions of these substances: the new net cleansing companies will have to adapt themselves to the new law from January of 2001, the old companies will have a period term for adapting themselves until 2005. These restrictions and limitations, have caused billionaire losses in the international shipping industry, resulting in an urgent necessity of manufacturing effective "anti-biofouling" technologies for replacing those paints containing toxic heavy metals and which would not exhibit environmental risks for the human health.

On the other hand, there are some products that use the nature as the source of the chemicals, which can be used both in anti-biofouling paints as in plastics, however, although nowadays some of them are in the market, there still is necessary more research on this subject, since many are the substances which have a potential use in preventing biofouling. The major part of these research projects or products are based in the fact that, many sessile aquatic organisms are free of biofouling, since they exhibit natural mechanisms as the production of metabolites with anti-fouling properties, at the level of affording protection against the colonization, reducing the competitiveness for the space in competitive environments. Also there are bacteria, mainly those of the *Pseudoalteromona* genus, which produce high molecular weigh substances with toxic and inhibitory properties for gram positive and gram negative bacteria. Until today, the bacterial specie *Pseudoalteromona tunicate*, has been widely studied regarding the production of a variety of extra-cellular components, which are responsible of inhibiting the settlement of common organisms of biofouling, such as bacteria, fungus, benthic microalgae, algae spores and marine invertebrates.

Some research projects developed for FONDEF (Fondo de Fomento al Desarrollo Científico y Tecnológico: Funds for the Promotion of the Scientific and Technologic Development) in our laboratory have allowed to isolate and identify a marine bacteria named as Ni1 LEM, which corresponds to an *Alteromonas* sp, which on laboratory in vitro studies and on the subsequent in situ studies, on the marine environment have shown the ability of significantly diminishing the settlement and fixing percentage, of the main components of the "biofouling" without affecting the culture organisms of commercial importance, further of being harmless for the environment.

SUMMARY OF THE INVENTION

One of the main objects of the present invention is to inhibit the settlement and fixing of the main organisms which are part of the "Biofouling", mainly benthic microalgae (diatomeae), macroalgae and larvae of marine invertebrates.

According to the invention the objective is achieved providing bioactive substances, from the artificially cultured marine bacteria *Alteromonas* sp (Ni1 LEM), which (the substances) are applied and adhered to the fixing substrates of those organisms belonging to the "biofouling" group.

In a preferred embodiment, the present invention, is related to an extra-cellular product, which acts as a anti-biofouling agent against common biofouling marine invertebrates, wherein the product comprises an extract from the supernatant of the *Alteromonas* sp Accession No NRRL B-30784 culture, wherein said extract is formed by the supernatant of said *Alteromonas* sp culture, which has been submitted to different treatments, among which are comprised filtering through membranes, or heating the extract, or the dialysis of said extract.

In an additional embodiment, the present invention is related with an anti-biofouling composition, which is formed by the extra-cellular product treated or without treatment according to the above, with a biopolymer, in order to form a gel comprising the product and which allows its controlled release into the environment wherein it is desirable to inhibit or prevent the adherence or fixation of the micro-biofouling or macro-biofouling. The biopolymer to be used can be selected from sources of commercially available biopolymers, being preferable the following commercially available biopolymers as Alginate, Phytagel®, Gelrite®, Nobel Agar®, Agargel®, Transfergel®. Being Phytagel® the most preferred biopolymer.

Said composition, in the form of a gel comprises said extra-cellular product in a rate (v/v) comprised in the range from about 1:2 to about 1:10, being preferable the composition comprising the extra-cellular product in a rate comprised in the range from about 1:2 to about 1:5, being the most preferred a composition comprising the extra-cellular product in a rate of 1:2, based in the final volume of the composition.

In an additional embodiment, the present invention is related to the use of said anti-biofouling extra-cellular product for preparing a composition, which is useful for avoiding or inhibiting the micro-biofouling and the macro-biofouling, wherein said macro-biofouling phenomena are produced by the fixing or adherence of one or more marine invertebrates and/or macroalgae, per example, as those organisms selected from the group formed by *Ulva lactuca, Pyura praeputialis, Ciona intestinalis*, and *Semimytilus algosus*, and wherein said micro-biofouling are produced by the fixing or adherence of one or more organisms or the type of benthic microalgae or diatomaceous, per example, as those selected from the group formed by *Nitzschia* sp1, *Amphora* sp, *Cylindroteca closterium, Nitzschia ovalis amott, Chaetoceros minutissimus, Navícula* sp1, *Navícula* sp2, and *Nitzschia* sp2.

In an additional embodiment, the present invention relates to a process for preparing said anti-biofouling extra-cellular product, which comprises the steps of isolating the supernatant from the *Alteromonas* sp Accession No NRRL B-30784 culture, and the subsequent filtration or ultra-filtration of the obtained supernatant. Optionally, said preparation process comprises the additional step of heating the supernatant, at a temperature comprised between about 70° C. and 100° C., during about 20 minutes, being preferable a heating at a temperature comprised between about 90 to 100° C., being more preferable the heating at 100° C.

In the process for obtaining the anti-biofouling extra-cellular product of the present invention, in an optional way, a supernatant dialysis step can be carried out, through a dialysis membrane having an exclusion size comprised between 3,500 da and 10,000 da. Being preferable the dialysis through a membrane which exclusion size is of 3,500 da.

In an additional embodiment, of the process for obtaining the anti-biofouling extra-cellular product of the present invention, the above obtained dialysate is submitted to a concentrating step, either dialyzed through the 10,000 da membrane or the 3,500 da membrane, wherein said concentrating step is carried out until a dialysate and concentrated product, between 2 to 30 times, is obtained, or it is concentrated between 5 to 25 times, being preferable a concentrating of the dialysate of 20 times. Further, said concentrated can be used according to the objective described in the present application and/or for preparing the anti-biofouling composition, with a biopolymer.

DETAILED DESCRIPTION OF THE INVENTION

The following experimental protocols, describe the preferred embodiments of the invention, and should not be considered as limiting the scope of the present invention.

On the other hand, a skill in the art should be able of carrying out the appropriate modifications, or to use alternative techniques, which are known in the state of the art, for carrying out the experiments with the same final objective of the invention.

In the present invention, the term "SSM", means a Marine Saline Solution, which corresponds to solution comprising a mixture of NaCl, KCl and $MgSO_4$ en a proportion of 24:1:8, dissolved in a volume of distilled water (1 L), with a pH value of 7.0, and autoclaved.

In the present invention, the term "Sw", means "Sea water", comprised of sea water which is submitted to a filtration through 0.45 µm and which subsequently is autoclaved.

Experimental use of the Extra-Cellular Bioactive Substances of Marine Bacteria in the Laboratory Isolation of marine bacteria with potential anti-biofouling activity The selected bacteria, which exhibit "anti-biofouling" ability, were isolated from artificial and natural substrates, which exhibited a significantly low colonization of "macro-biofouling", regarding other adjacent substrates.

Artificial Substrates

In the case of an artificial substrate, an area of 1 cm² was delimited, aseptically rubbing the film adhered on the same. The obtained rubbing, was laid on containers comprising 10 ml of sterile saline marine solution (SSM). Further, a little piece of the substrates was selected; it was repeatedly washed with sterile sea water and laid on a container with 10 ml of sterile SSM. Subsequently, the rubbing and/or the piece of substrate, was submitted, during 60 seconds, to ultrasound treatments in order to obtain a suspension containing the associated microorganisms.

Natural Substrates

Those marine invertebrates, algae, sponges and cnidaries, wherein the outer surface of them was free of "macro-biofouling", were selected and immediately transported to the Laboratorio de Ecología Microbiana de la Universidad de Antofagasta (Marine Microbial Ecology Laboratory of the Universidad de Antofagasta). Subsequently, these were repeatedly washed with sterile sea water and through the use of sterile dissection material, a tissue sample was removed from the surface. The recovered tissue was homogenized with 10 ml of sterile SSM, by means of a Stomacher homogenizer.

For seeding the samples and maintaining the microorganisms the following procedure was used:

For isolating the associated bacterial flora, were carried out suitable dilutions of each sample, which were seeded in plates with the following culture media: (1) agar tryptone complemented with 2% NaCl (TSA2, Oxoid Co.), (2) agar Pseudomona (AP, Oxoid Co), (3) Zobell marine agar 2216 (AM, Difco Co.), (4) Nine salts agar V (VNSS, Albertson et al. 1990) and (5) thiosulfate-citrate-biliary salts-sucrose agar complemented with 2% NaCl (TCBS2, Oxoid Co.). Following the agar plates seeding and the culturing during one week at 20° C. the dominant morphotypes (habitus) were isolated for its later characterization through general bacterial identification methods (Hansen & Sorheim 1991 Seeley et al. 1995, Gerhardt et al. 1994, Holt et al. 1994). Regarding the isolated bacterial species, these were maintained under ultra-refrigeration (−80° C.) on tryptone broth (TSB, Oxoid Co.) complemented with 2% NaCl.

Experimental Protocole 1: Effect of Bacterial Extra-Cellular Products on the Fixation of Common "Biofouling" Diatomeaceous is Illustrated in FIGS. 1 to 8.

The objective of the present experiment, intends to quantify and evaluate the effect of bacterial extra-cellular products on the fixation of the diatomea unialgal cultures, which form the common fixation substrate of the scallop (*Argopecten purpuratus*) and abalone (*Haliotis discus hanai*) seeds, in a polystyrene substrate, and for preliminary characterizing the nature of the product.

Microalgae to be used: *Nitszchia* sp1 (Nc), *Amphora* sp (Nv), *Nitzschia ovalis arnott* (Fp), *Cylindroytheca closterium* (Cc), *Chaetoceros minutissimus* (Nm), *Navicula* sp1 (Nav sp1), *Navícula* sp2 (Nav sp2) and *Nitzschia* sp2 (Nitz sp2).

Bacterial Products to be used: Bacterial extra-cellular products from 3 periphytic bacteria which exhibited activity against "micro-biofouling": *Pseudoalteromona tunicata* (Pt) (collection Strain), *Halomonas marina* (Hm) (collection Strain), *Alteromona* sp (Nil LEM). Additionally, as the positive control the marine bacteria *Halomonas* sp (NC1), was used.

Obtaining of the extra-cellular products: Were cultured, bacteria which exhibited inhibitory activity over micro-biofouling, in 1 liter of minimum culture media (M9) until stationary phase at room temperature. The bacterial supernatants were collected using centrifugation at 11,000 rpm×15 minutes, hey were sterilized through double filtration at 0.22 μm. Subsequently, the obtained supernatant was divided into 6 parts, to which the following treatments were applied:

1. Supernatant A: Supernatant without any treatment. (Pt, Hm, Nil LEM y NC1).
2. Supernatant B: Supernatant heated at 100° C. during 20 minutes. (Pt, Hm, Nil LEM).
3. Supernatant C: Supernatant dialyzed at 3,500 da. (Nil LEM).
4. Supernatant D: Supernatant dialyzed at 10,000 da. (Nil LEM).
5. Supernatant E Supernatant dialyzed at 3,500 da, concentrated. (Nil LEM).
6. Supernatant F: Supernatant dialyzed at 10,000 da concentrated. (Nil LEM).

Regarding the controls these were: Control Sea water (Sw) and minimum media control (M9).

Microalgae inoculation Concentration: 3.5×105 cells×ml-1.

Duration of the Experiment: 24 hours.

Volume by well: 0.2 ml (supernatant 0.1 ml and 0.1 ml of diatomea culture previously washed with autoclaved Sw 0.45 □m, for removing any effect of the microalgal culture media F/2 (Guillard, 1975).

Process: Polystirene multiwell Plates of 6 mm diameter were gauged with 0.1 ml of a microalgal culture from pre-stationary phase cultures, further 0.1 ml of bacterial supernatant (according to the treatment) with a total first concentration of 3.5×105 cells×ml-1 (2.5×105 cells× cm-2), then they were maintained in a controlled environment room at 20° C. with a photoperiod of 12:12 hours. The microalgae counts were carried out at 24 hours from incubating. Once, the incubation time was completed, the multiwell plates were washed 5 times with autoclaved Sw, then using an en un inverted microscope with 100× magnification, the adhered microalgae count is carried out. The results were expressed as cells× $cm^{-2}$.

Sw Control Sea water control.
M9 Control: minimum media Control.
100° C.=Extra-cellular Products treated at 100° C.
Sob: Supernatants without treatment.
>3.500: Supernatants dialyzed at 3,500 Da.
>10.000: Supernatants dialyzed at 10,000 Da.
[3.500]: Supernatants dialyzed at 3,500 Da and concentrated.
[10.000]: Supernatants dialyzed at 10,000 Da and concentrated.

The results by bioactive extra-cellular bacterial products are:

*Pseudoalteromona tunicata* (Pt): inhibitory effect on the 8 tested diatomeae, thermostable.

*Halomonas marinas* (Hm): inhibitory effect on 6 diatomeae, excepting *Amphora* sp and *Navícula* sp1, thermostable.

*Halomonas* sp (NC1): without inhibitory activity.

*Alteromonas* sp (Nil LEM): inhibitory effect on the 8 tested diatomeae, thermostable, it exhibits a molecular weight higher or equal to 3,500 dalton.

Conclusion

Based on the initial characterization showed in this experiment, the anti-microalgae component produced by *Alteromonas* sp (Nil LEM) has a low molecular weight, it is thermostable, it is water soluble then it can be efficiently released from bacterial biofilms on surfaces in the marine environment. The use of these substances has a potential application for preventing the fixation of one of the first links in the "biofouling" formation.

Figure 9:
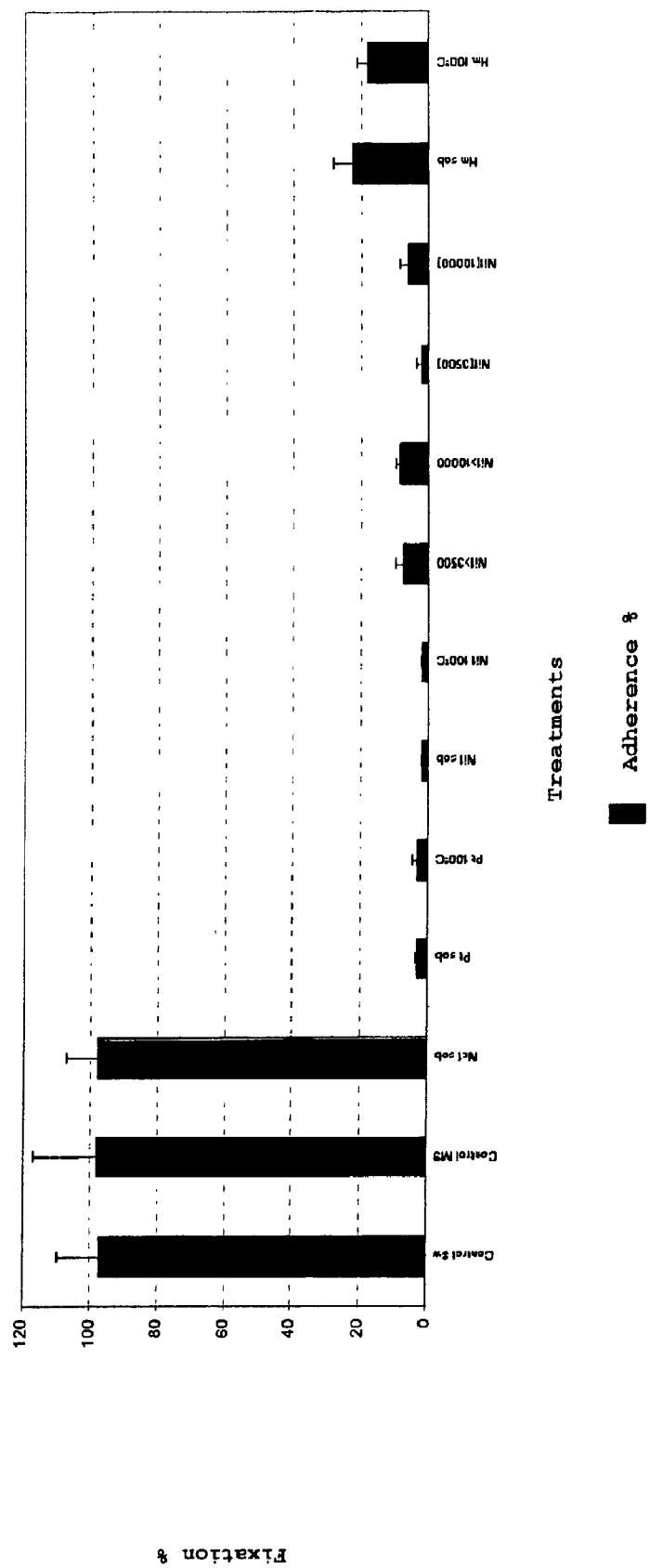

Experimental Protocol 2: Effect of the Bacterial Extra-Cellular Products on the Fixation of the Macroalga *Ulva lactuca* is Illustrated in FIG. 9.

1. *Ulva lactuca* samples were collected, previously to the sporulation (the algae must have the edge green brownish, verifying in a microscope the reproductive cells conditions [sporophyte or gametophyte])
   Sporophyte→the spores have 4 flagellum.
   Gametophyte→the male and female gametes have 2 flagellum
2. The algae were washed with abundant sea water (Sw) filtered through 0.45 □m and autoclaved.
3. The algae were dried during two hours at room temperature, in the presence of natural or artificial light.
4. The algae were placed in a beaker with autoclaved Sw 0.45 µm (1 algae per beaker of 200 or 500 ml). This beaker is placed near an artificial light source (desk lamp). Optionally, instead of placing the complete alga in the beaker, it can be selected (cutting) those area of the algae wherein the spores can be found.
5. Those spores found near the light source, were collected, and they were placed in a side of a 10 cm diameter clock glass diameter with autoclaved Sw 0.20 µm (on the opposite side of the light source). After 5-10 minutes were extracted those spores which have reached the other side of the clock glass. This step was repeated in order to be sure that the spores were free de of any associated microorganism.
6. The spores were collected and, and were added on 10 ml of autoclaved Sw 0.20 µm. The spores counting was carried out in a neubauer chamber (cells×ml$^{-1}$)
7. An amount of about 2,800 spores per well (multi-well chambers each of 6 mm diameter).
   Well area 0.28 cm$^2$→2.8×10µ$^2$.
   If 2,800 spores are in 0.28 cm$^2$→10,000 spores are in 1 cm$^2$.
   Volume by well 200 µl→2,800 spores.
   1,000 µl→14,000 spores.
8. Subsequently it was incubated at room temperature, during two hours in darkness, in order to allow the settlement of the spores.
9. It was incubated during 10-15 hours at room temperature, and under natural light, and then it was observed under inverse microscope in order to be sure that the spores have not germinated.
10. The Sw of the wells was removed and the fixed spore counting was carried out.
    Bacterial Products to be used: Bacterial extra-cellular products from 3 periphytic bacteria with activity against micro-biofouling: *Pseudoalteromona tunicata* (Pt), *Halomonas marina* (Hm), *Alteromona* sp (Nil LEM). Additionally, the supernatant of the bacteria *Halomonas* sp (NC1) was used as a positive control, since it does not have a negative effect against diatomeae.
    Obtaining of extra-cellular products: Bacteria exhibiting inhibitory activity for micro-biofouling, were cultured in 1 liter of minimum culture media (M9) until the stationery phase was reached, at room temperature. The bacterial supernatants were harvested by centrifugation at 11,000 rpm×15 minutes, sterilized using double filtration at 0.22 µm. Then, said obtained supernatant is divided in 6 portions to which will be carried out the following treatment:
    1. Supernatant A: Supernatant without treatment. (Pt, Hm, Nil LEM and NC1).
    2. Supernatant B: Supernatant treated at 100° C. during 20 minutes (Pt, Hm, Nil LEM).
    3. Supernatant C: Supernatant dialyzed at 3,500 da. (Nil LEM).
    4. Supernatant D: Supernatant dialyzed at 10,000 da. (Nil LEM).
    5. Supernatant E: Supernatant dialyzed at 3,500 da Concentrated. (Nil LEM).
    6. Supernatant F: Supernatant dialyzed at 10,000 da Concentrated. (Nil LEM).
    Regarding the controls, these will be: Control Sw and Control M9.
    Control Sw: Sea water Control.
    Control M9: Minimum media Control.
    100° C.=Extra-cellular Products treated at 100° C.
    Sob: Supernatants without treatment.
    >3.500: Supernatants dialyzed at 3,500 Da.
    >10.000: Supernatants dialyzed at 10,000 Da.
    [3.500]: Supernatants dialyzed at 3,500 Da and concentrated.
    [10.000]: Supernatants dialyzed at 10,000 Da and concentrated.

The results by bioactive extra-cellular products are:
*Pseudoalteromona tunicata* (Pt): Inhibitory effect of the fixation of *Ulva lactuca*, thermostable.
*Halomonas marinas* (Hm): Inhibitory effect of the fixation of *Ulva lactuca*, thermostable.
*Halomonas* sp (NC1): Without inhibitory activity.
*Alteromonas* sp (Nil LEM): Inhibitory effect of the fixation of *Ulva lactuca*, thermostable and with a molecular weight higher or equal to 3,500 dalton.

Conclusion

Based on the initial characterization showed in this experience, the inhibitory component of the fixation of the cosmopolitan macroalga *Ulva lactuca* produced by *Alteroinonas* sp (Nil LEM) has a low molecular weight, it is thermostable, water soluble and can be efficiently released and transported in the marine environment. The use of these substances has a potential application for preventing the fixing of this common "biofouling" macroalga.

Figure 10:
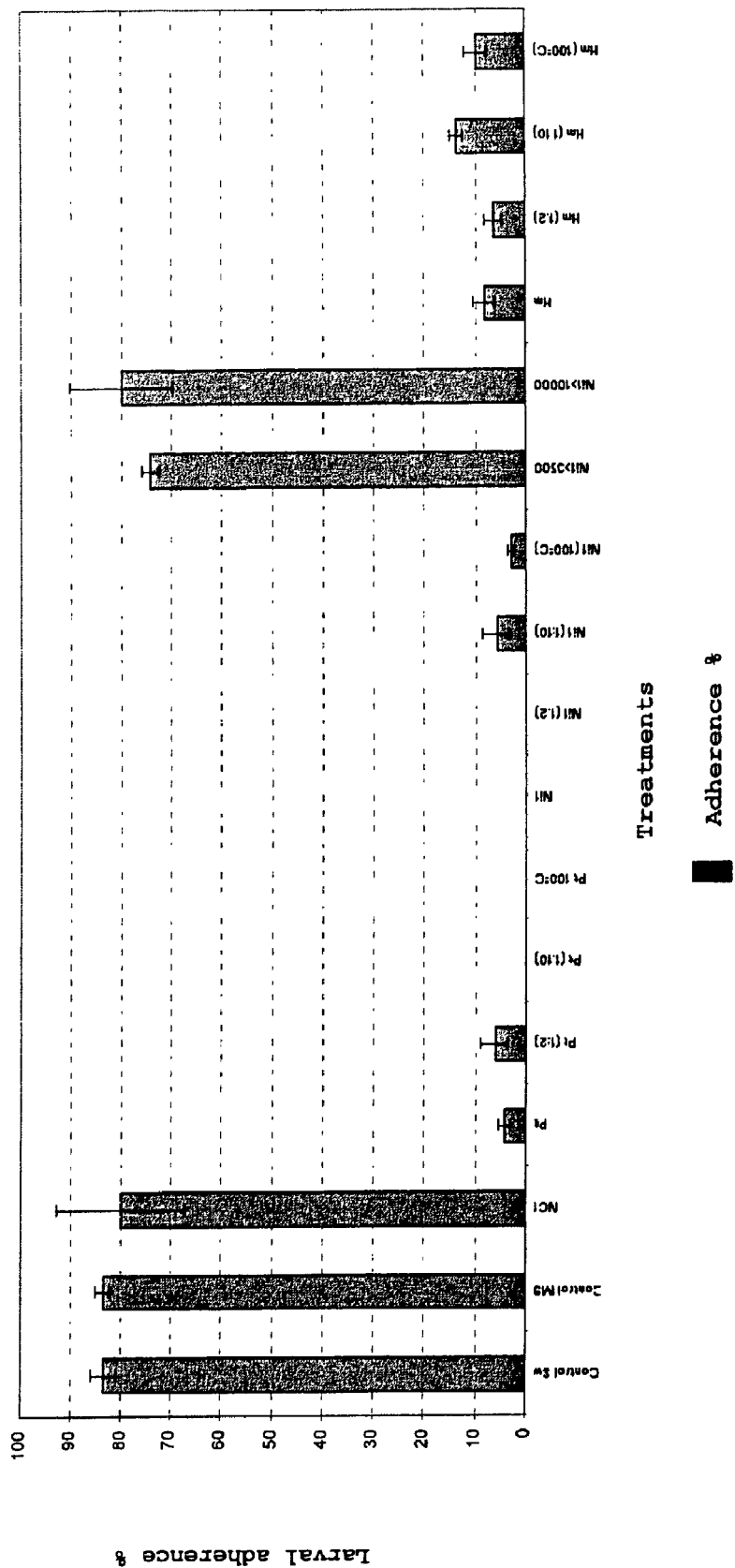

Experimental Protocol 3: Effect of the Bacterial Extra-Cellular Products on the Fixing of *Ciona intestinalis* larvae is Illustrated in FIG. 10.

The objective of the present experiment was to quantify and assess the effect of the bacterial extra-cellular products over the fixing of larvae from *Ciona intestinalis* on a polystyrene substrate.
    Bacterial Products to be used: Bacterial extra-cellular products from 3 periphytic bacteria which exhibit activity against micro-biofouling: *Pseudoalteromona tunicata* (Pt), *Halomonas marina* (Hm), *Alteromona* sp (Nil LEM). Additionally the supernatant of the bacteria *Halomonas* sp (NC1) was used as positive control, since it does not show a negative effect against diatomeae.
    Obtaining the extra-cellular products: Bacteria exhibiting inhibitory activity against "micro-biofouling" were cultured in 1 liter of minimum culture media (M9) until is reached the stationary phase, at room temperature. The bacterial supernatants were harvested by centrifugation at 11,000 rpm×15 minutes, sterilized through double filtration at 0.22 μm. Then, this obtained supernatant is divided in 6 portions, to which the following treatments will be applied:
1. Supernatant A: Supernatant without treatment.
2. Supernatant B: Supernatant diluted in Sw 1:2
3. Supernatant C: Supernatant diluted in Sw 1:10
4. Supernatant D: Supernatant heated at 100° C. during 20 minutes.
5. Supernatant E: Supernatant dialyzed at 3,500 da.
6. Supernatant F: Supernatant dialyzed at 10,000 da.

Regarding the controls, this will be: Sea Water Control (Sw) and Minimum media Control (M9).

Duration of the Experiment: 48 hours.

Volume per well: 3 ml.

Process: The selected bacterial strains were growth with stirring in one liter of VNSS broth during 24 hours at room temperature. The cells were centrifuged at 13,200 g during 30 minutes at 10° C. and the supernatant was discarded. The supernatant was collected and filtered at 0.22 μm for the further use of said supernatants, in the bioassays with *Ciona intestinalis* larvae. The crude supernatant was tested with said larvae, the different dilutions of the same (1:2; 1:10), the dialyzed treatment at 3,500 and 10,000 dalton were assayed with these larvae (in an amount of 25-30 larvae per well of the multiwell chamber), they were combined, and then were incubated during 48 hours in darkness. As control, bioassays without incorporating the cellular supernatant, were carried out (only with sea water and minimum media (M9)). The larvae counts were carried out (fixed larvae) in an inverted microscope with a 100× magnification.

Control Sw: Sea Water Control.
Control M9: minimum media control.
100° C.=Extra-cellular products treated at 100° C.
Sob: Supernatants without treatment.
>3.500: Supernatants dialyzed at 3,500 Da.
>10.000: Supernatants dialyzed at 10,000 Da.

The results per bioactive bacterial extra-cellular products are:
*Pseudoalteromona tunicata* (Pt): Inhibitory effect of the fixing of *Ciona intestinalis*, thermostable.
*Halomonas marinas* (Hm): Inhibitory effect of the fixing of *Ciona intestinalis*, thermostable.
*Halomonas* sp (NC1): without inhibitory activity.
*Alteromonas* sp (Ni1 LEM): Inhibitory effect of *Ciona intestinalis*, thermostable, with a molecular weight minor or equal to 3,500 dalton.

Conclusion

Based on the initial characterization showed in this experience, the antilarva component produced by *Alteromonas* sp (Ni1 LEM) has a low molecular weight, is thermostable, water soluble and can be efficiently released and transported into the marine environment. The use of these substances has a potential application for preventing the fixing of one of the common components of "macro-biofouling".

Figure 11:
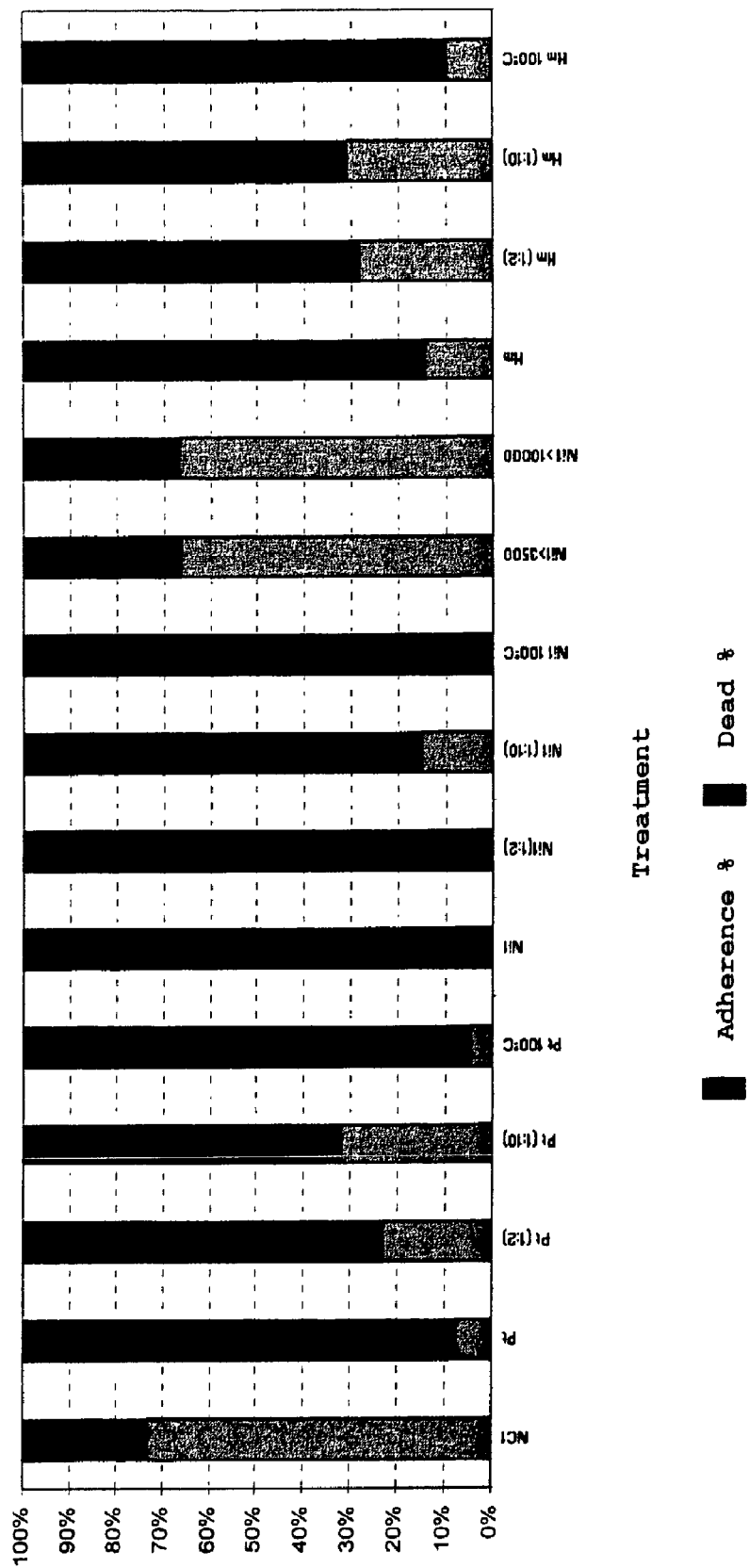

Experimental Protocol 4: Effect of the Bacterial Extra-Cellular Products on the Fixing of Larvae of *Pyura praeputialis* is Illustrated in FIG. 11.

The objective of the present experiment was to quantify and assess the effect of the bacterial extra-cellular products over the fixing of larvae of *Pyura praeputialis* in a polystyrene substrate.

Bacterial Products to be used: Bacterial extra-cellular products from 3 periphytic bacteria which exhibit activity against micro-biofouling: *Pseudoalteromona tunicata* (Pt), *Halomonas marina* (Hm), *Alteromona* sp (Ni1 LEM). Additionally the supernatant of the bacteria *Halomonas* sp (NC1) was used as positive control, since it does not have a negative effect against diatomeae.

Obtaining the extra-cellular products: Bacteria which exhibited inhibitory activity against "micro-biofouling", were cultured in liter of minimum culture media (M9) until the stationary phase is reached at room temperature. The bacterial supernatants were harvested by centrifugation at 11,000 rpm×15 minutes, sterilized through double filtration at 0.22 μm. Then, the obtained supernatant is divided in 6 portions, to which the following treatments will be applied:
1. Supernatant A: Supernatant without treatment.
2. Supernatant B: Supernatant diluted in Sw 1:2
3. Supernatant C: supernatant diluted in Sw 1:10
4. Supernatant D: Supernatant treated at 100° C. during 20 minutes.
5. Supernatant E: Supernatant dialyzed at 3,500 da.
6. Supernatant F: Supernatant dialyzed at 10,000 da.

Regarding the controls, these will be: Sea Water Control (Sw) and Minimum media Control (M9).

Duration of the Experiment: 24 hours.

Volume per well: 3 ml.

Process: The selected bacterial strains were cultivated, with stirring, in one liter of VNSS broth during 24 hours at room temperature. The cells were centrifuged at 13,200 g. during 30 minutes at 10° C. and the supernatant was discarded. The supernatant was collected and filtered at 0.22 μm for the subsequent use of said supernatants in the bioassays with *Pyura praeputialis* larvae. The crude supernatant was tested with said larvae, the different dilutions of the same (1:2; 1:10) and the dialyzed treatment at 3,500 and 10,000 dalton were assayed with these larvae (in an amount of 20-25 larvae per well of the multiwell chamber), they were combined and then incubated during 24 hours in darkness. As control, bioassays without incorporating the cellular supernatant were carried out (only with sea water and minimum media (M9)). The fixed larvae counts were carried out in an inverted microscope with a 100× magnification.

Control Sw: Sea Water Control.
Control M9: minimum media control.
100° C.=Extra-cellular products treated at 100° C.
Sob: Supernatants without treatment.
>3.500: Supernatants dialyzed at 3,500 Da.
>10.000: Supernatants dialyzed at 10,000 Da.

The results per bioactive bacterial extra-cellular products are:
*Pseudoalteromona tunicata* (Pt): Inhibitory effect of the fixing of *Pyura praeputialis*, thermostable.
*Halomonas marinas* (Hm): Inhibitory effect of the fixing of *Pyura praeputialis*, thermostable.
*Halomonas* sp (NC1): without inhibitory activity.
*Alteromonas* sp (Ni1 LEM): Inhibitory effect of *Pyura praeputialis*, thermostable, with a molecular weight minor or equal to 3,500 dalton.

Conclusion

Based on the initial characterization showed in this experience, the antilarvae component produce by *Alteromonas* sp (Ni1 LEM) has a low molecular weight, it is thermostable, water soluble and can be efficiently released and transported into the marine environment. The use of these substances has a potential application for preventing the fixing of this common "biofouling" component.

Figure 12:
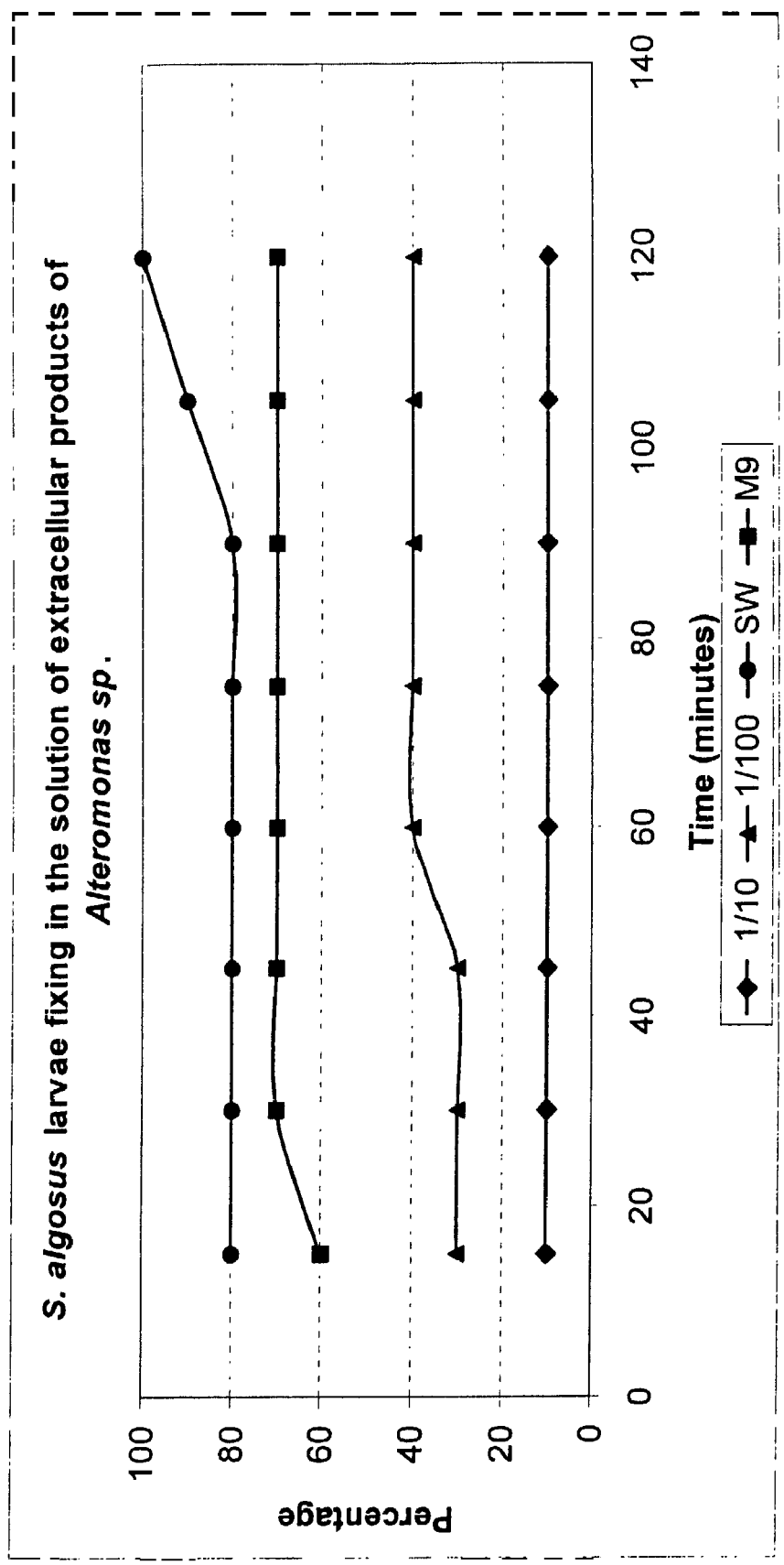

Experimental Protocol 5: Effect of the Bacterial Extra-Cellular Products on the Fixing of Larvae of the Mussel *Semimytilus algosus* is Illustrated in FIG. 12.

The objective of the present experiment, was to quantify and assess the effect of the bacterial extra-cellular products of the strain *Alteromonas* sp (Ni1 LEM) on the fixing of larvae from *Semimytilus algosus* on a polystyrene substrate.

Obtaining the extra-cellular products: The bacterial extra-cellular products were obtained culturing the bacteria in M9 broth (Minimal Médium: Casamino acids 1 g, $Na_2HPO_4$ 6 g, $KH_2PO_4$ 3 g, $NH_4Cl$ 1 g, NaCl 21 g. The pH was adjusted to 7.1, and complemented with a source of 0.0065% carbon, 10 ml of 0.1M $MgSO_4 \times 7 H_2O$; 10 ml of 0.01 M $CaCl_2 \times 2 H_2O$ and B1 al 1%) during 120 hours, in 1 L bottles. Then, the media was centrifuged at 11,000 rpm during 15 minutes. Subsequently, the supernatant was collected in 2 L schott bottles, which after were frozen at $-20°$ C.

Figure 13:
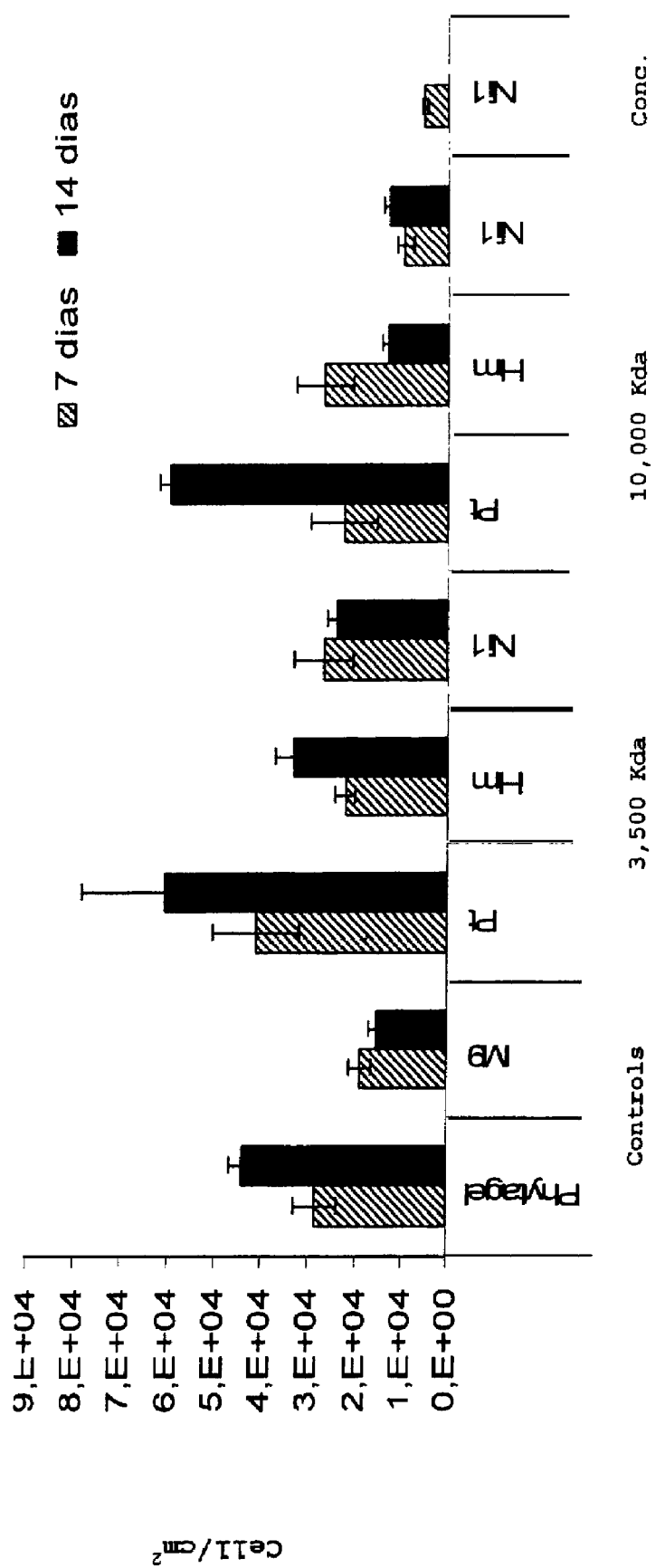
Figure 14:
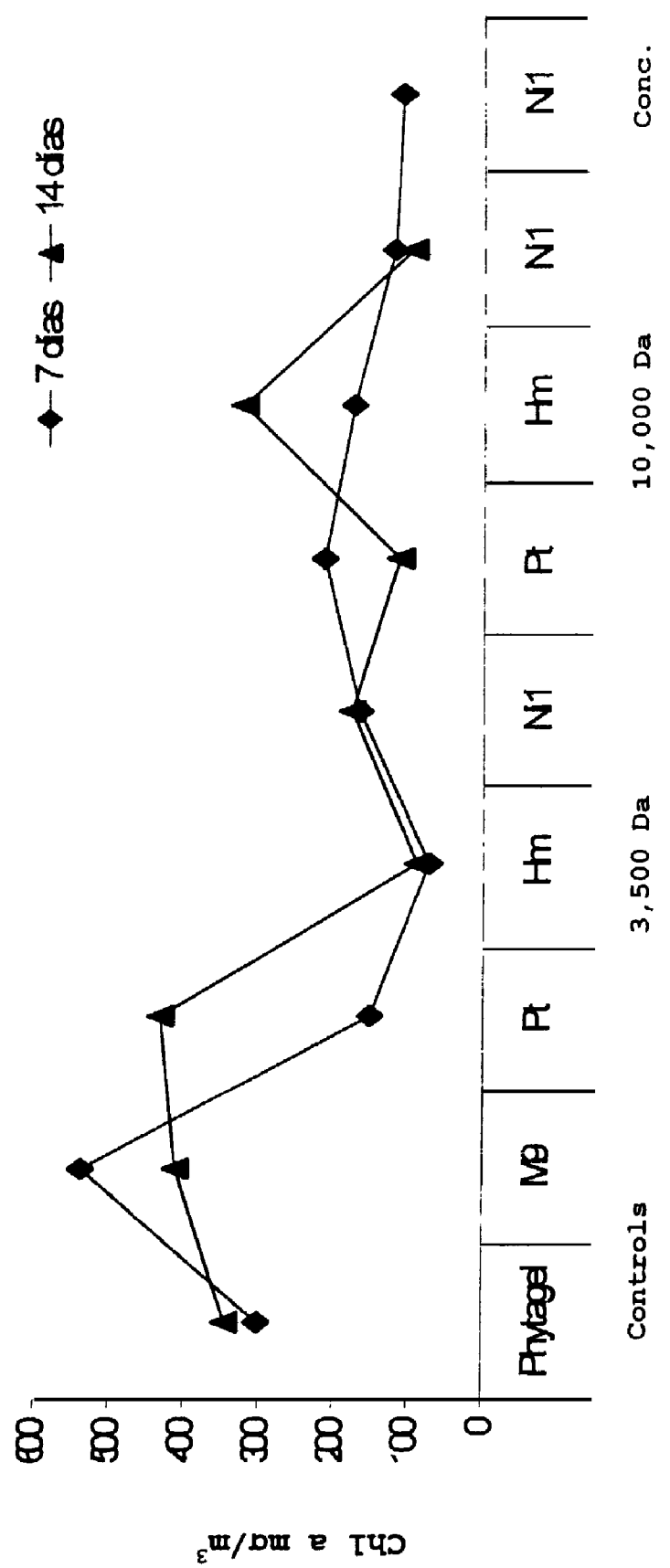

Monitoring of the Fixing of *Semimytilus algosus* Exposed to the Extra-Cellular Products Solution:

FIG. 13 shows the microfouling in situ coverage during 7 and 14 days of the 3,500 and 10,000 kDa dialysed extra-cellular products from the Pt, Hm and Ni1 bacteria. FIG. 14 shows the presence of Chlorophyll a biomass in the in situ microfouling during 7 and 14 days in a phytagel matrix with 3,500 and 10,000 Da dialyzed extra-cellular products from the bacteria Pt, Hm and Ni1.

The objective of the present experiment is to determine the in situ inhibition of epibiontic microorganisms, by extra-cellular products from marine bacteria.

Bacterial Products to be used: Products obtained from the marine bacteria *Pseudoalteromonas tunicata* (Pt), *Halomonas marina* (Hm) and *Alteromonas* sp (Ni1 LEM).

Obtaining the extra-cellular products:

The marine bacteria (Pt, Hm y Ni1 LEM) were cultured during the night, in Triptone Soja culture Broth (TSB) at room temperature with stirring (60 rpm). The bacteria were inoculated in 1 L of minimum media (M9) at a concentration of $1*10^6$ cell/ml which contained 500 g of sterile shells from *Turritella cingulata*, which were used as substrate for the bacterial culture, during 5 days. Considering that these bacteria have benthic life (adhered to any marine surface). The products, were collected through centrifugation at 10,000 rpm during 15 min. After that, they were filtered at 0.2 µm and subsequently dialyzed at 3,500 or 10,000 Da during 24 hours.

Duration of the experiment: Fourteen days.

Process: The products which were dialyzed at 3,500 and 10,000 Da of each bacteria were combined in Phytagel® over 6 polycarbonate films (2.5×7.5 cm) and diluted ⅟10. For the controls, the products were replaced by distilled water and M9, furthermore, a 20× concentrated of the bacteria Ni1 LEM was added in a rotavapor at 75° C. during 30 minutes only until 7 days. The films were placed in an acrylic container weighting 3 Kg, so they can be maintained submerged in the sub-tide zone in a Pacific coast beach. # films were removed at the 7 and 14 day of each treatment. After that, the films that were removed from the sea were placed on a Petri plate and were observed in the inversed microscope (Olympus IX 50) with a total 200× magnification. Capturing photographs of the films in a clear field microscope (Olympus BX 51) and finally the chlorophyll a analysis was determined using the Jeffrey and Humphrey equation (1975) in a spectrophotometer (ANTHLIE Advanced).

Results

From the three strains used in the study, the Extra-cellular Products (PE) from Ni1 LEM, dialyzed at 10,000 Da showed the minor coverage of micro-biofouling at the days 7 and 14, with $9.4 \times 10^3$ and $1.26 \times 10^4$ cells/cm2, while Hm was of $1.3 \times 10^4$ respectively. The Chl a biomass in Hm dialyzed at 3,500 Da at day 7 was of 72.56 Chl a mg/m3, in turn at the day 14 were obtained the lower values in the treatments with Hm dialyzed at 3,500 Da and Ni1 LEM dialyzed at 10,000 Da, with values of 88.55 and 93.77 Chl a mg/m$^3$ Conclusion The results show a strong in situ inhibition of epibiontic microorganisms of the PE from *Alteromonas* sp (Ni1 LEM) and *Halomonas marina* (Hm) using dialyzates of 10,000 Da.

Figure 15:
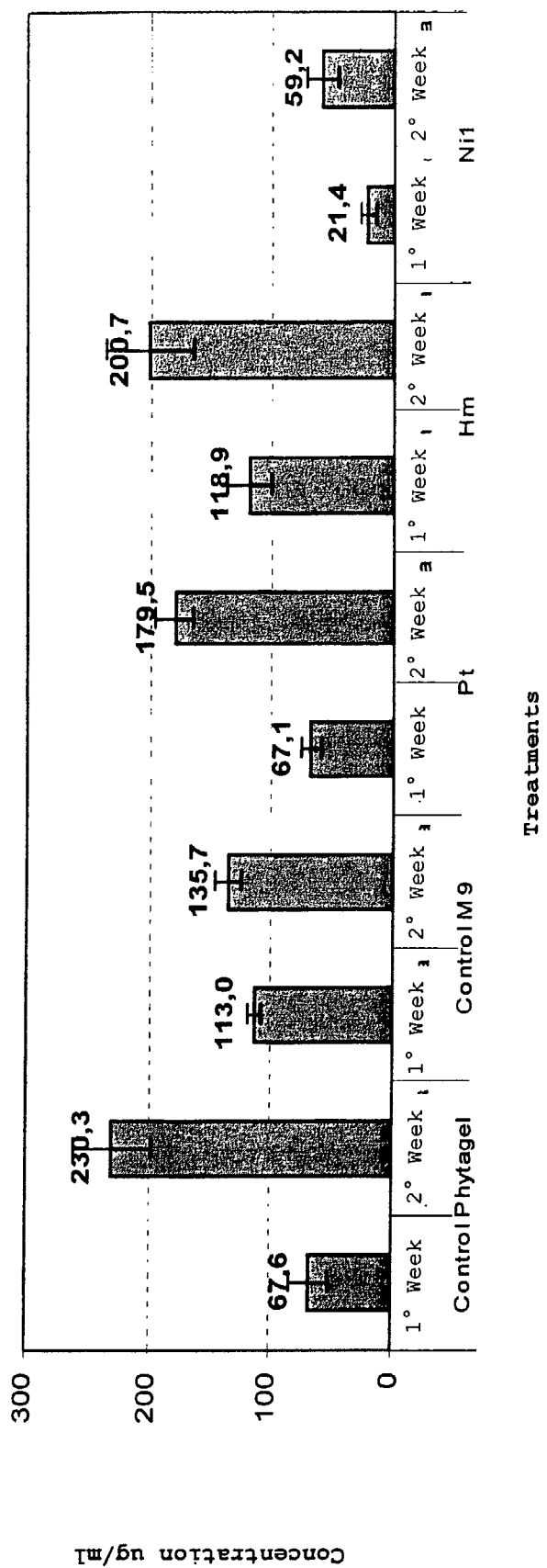

Experimental Protocol 7: Effect of the Bacterial Extra-Cellular Products on Fixed in Phytagel® over the "Micro-Biofouling" in FIGS. 15 and 16.

Objectives:
1. To assess the effect of marine bacteria over the growing of the "micro-biofouling."
2. To preliminary determine the bacterial extract with the higher "anti-biofouling" activity.

Bacterial Extra-Cellular Products to be Used:
1. *Pseudoalteromona tunicata* (Pt)
2. *Halomona marina* (Hm)
3. Ni1-LEM (*Alteromonas* sp)

Obtaining the Extra-Cellular Products:

The extra-cellular fractions were obtained from the bacterial strains Pt, Hm, Ni1-LEM. These were cultured until the stationary phase in minimum media (M9) with constant stirring at room temperature. Subsequently, they were centrifuged at 11,000 rpm during 15 minutes at 4° C., and the supernatant or extra-cellular fraction was filtered twice at 0.2 µm, and stored at $-20°$ C.

Inert Matriz Preparation:

For controlling the adherence to the matrix, 0.326 g of Phytagel®, were diluted in 20 ml of nuclease free water, using an electric mixer. The mixture was heated during 60 s in a microwave oven. At the same time, the extracts are heated and maintained in a water bath at 45-50° C., then they are added to the Phytagel® solution at a 1:10 dilution. The matrix with the extracts is disposed into polystirene plates of 30 mm diameter, for preparing tablets, which once solidified are removed from the plates, and placed in a 1.000 L tank with sea water and a constant flux of 1 L×15 seconds.

Duration of the Experiment: 14 days.

Process:
1. The Phytagel tablets containing the extracts, the M9 controls and the Phytagel controls were fixed on PVC tubes, which were submerged in the 1000 L tank with constant flux. The tablets with the extracts were recovered each week, as well as the respective controls. The weight of each one was registered before and after being exposed to the macro-biofouling, using an analytic scale Sartorius BP-221S. The results were registered as the adherence % of the organisms over the Phytagel® tablets.

The proteins concentration in the obtained bacterial extracts was measured, through absorption at 562 nm (BCA Protein Assay Reagent Kit, Pierce). For this purpose was used a SECOMAN spectrophotometer (Anthelie Advanced).

The percentage of adherence of the "micro-biofouling" during the first week, was maintained constant for all the treatments, being recorded for the second week a decrease for the tested bacteria and for the Phytagel® control, but not for the M9 control, which maintained a similar value regarding the first week. The extra-cellular products of the Ni1 LEM bacteria recorded the lower values during the experiment term.

Conclusion

The proteins concentration of the "micro-biofouling" that are fixed or adhered on the Phytagel® tablets containing the extra-cellular products of the Ni1 LEM bacteria, was the minor recorded value, showing 21.4 µg/ml for the first week and 59.2 µg/ml for the second week of the experiment.

The invention claimed is:

1. An extra-cellular anti-biofouling product, useful against biofouling by common marine invertebrates, comprising an extract from a supernatant of an *Alteromonas* species (sp.) culture having Accession Number (No.) NRRL B-30784.

2. An anti-biofouling composition, comprising an extract obtained from a supernatant of an *Alteromonas* sp. culture having Accession No. NRRL B-30784, and a biopolymer.

3. The anti-biofouling composition according to claim 2, wherein the extract is comprised in composition at a volumetric ratio of about 1:2 to 1:10, based on the final volume of composition.

4. The anti-biofouling composition according to claim 3, wherein the volumetric ratio is about 1:2 to 1:5.

5. The anti-biofouling composition according to claim 4, wherein the volumetric ratio is 1:2.

6. A process for preparing an anti-biofouling extra-cellular product comprising the steps of:
   a) isolating a supernatant from an *Alteromonas* sp. Accession No. NRRL B-30784 culture to obtain an isolated supernatant;
   b) filtering twice the isolated supernatant through a 0.22 µm membrane to obtain a filtered isolated supernatant, and recovering the anti-biofouling extra-cellular product.

7. The process according to claim 6, wherein the process further comprises a step of heating the filtered isolated supernatant obtained from step b) at 100° C. for 20 minutes.

8. The process according to claim 7, wherein the process further comprises a step of dialyzing the isolated supernatant obtained from the step a) through a dialysis membrane having an exclusion size in the range from about 3,500 Da to about 10,000 Daltons (Da) to form a dialysate.

9. The process according to claim 8, wherein the process further comprises a step of concentrating 20 times the dialysate.

10. The process according to claim 8, wherein the exclusion size is about 3,500 Da.

11. A product prepared according to the process of claim 6.

12. A product according to the heating step of claim 6.

13. A product according to dialyzing step of claim 7.

14. A product according to the concentrating step of claim 8.

15. The product according to claim 13, made further wherein the exclusion size is about 3,500.

16. The anti-biofouling composition according to claim 2 wherein the composition is useful against macro-biofouling produced by the fixing or adherence of one or more organisms selected from the group consisting of *Ulva lactuca, Pyura praeputialis, Ciona intestinalis,* and *Semimytilus algosus.*

17. The anti-biofouling composition according to claim 2 wherein the composition is useful against macro-biofouling produced by the fixing or adherence of one or more organisms selected from the group consisting of *Nitzschia* sp1, *Amphora* sp, *Cylindrotheca closterium, Nitzschia ovalis arnott, Chaetoceros minutissimus, Navicula* sp1, *Navicula* sp2, and *Nitzschia* sp2.

* * * * *